United States Patent [19]

Haber et al.

[11] 4,421,735

[45] Dec. 20, 1983

[54] RADIOLABELED DIAGNOSTIC COMPOSITIONS AND METHOD FOR MAKING THE SAME

[75] Inventors: Edgar Haber, Weston; Ban A. Khaw, Milton, both of Mass.

[73] Assignee: The Massachusetts General Hospital, Boston, Mass.

[21] Appl. No.: 141,053

[22] Filed: Apr. 17, 1980

[51] Int. Cl.³ .................... A61K 43/00; A61K 49/00; C07G 7/00

[52] U.S. Cl. ................. 424/1.1; 260/112 R; 424/9

[58] Field of Search .................. 424/1, 9; 260/112 R

[56] References Cited

U.S. PATENT DOCUMENTS

| | | | |
|---|---|---|---|
| 4,022,877 | 5/1977 | Huber et al. | 424/1 |
| 4,057,615 | 11/1977 | Bardy et al. | 424/1 |
| 4,057,617 | 11/1977 | Abramovici et al. | 424/1 |
| 4,094,965 | 6/1978 | Layne et al. | 424/1 |
| 4,250,161 | 2/1981 | de Schrijver | 424/1 |
| 4,272,503 | 6/1981 | Camin et al. | 424/1 |

OTHER PUBLICATIONS

*Principles of Radiopharmacology,* vol. I, Colombetti (Ed.), CRC Press, Inc., Boca Raton, Fla., 1979, pp. 262–264.

*Primary Examiner*—Christine M. Nucker
*Attorney, Agent, or Firm*—Paul J. Cook

[57] ABSTRACT

Protein molecules are covalently bonded to a chelating agent which in turn binds a radioactive molecule. Prior to binding, the radioactive molecule is reduced with dithionite ion and then mixed with protein at a pH of 7.0 to about 8.0.

14 Claims, No Drawings

RADIOLABELED DIAGNOSTIC COMPOSITIONS AND METHOD FOR MAKING THE SAME

BACKGROUND OF THE INVENTION

Biologically active macromolecules such as antibodies specific for myosin, carcinoembryonic antigen (CEA), alpha feto protein or human chorionic gonadotropin labeled with radioactive iodine such as iodine-125 or iodine-131 have been used both experimentally and clinically to localize and visualize target organs. Radioactive iodine isotopes are not ideal isotopes for scintigraphy due to their half-lifes and their peak energy of emission. The peak energy of emission of iodine-125 at 35 kev is too low for scintigraphy and peak energy of emission of iodine-131 at 364 kev is too high. The presence of beta emission also make these two radioiodine isotopes undesirable for clinical use. An isotope that is better suited for scintigraphy is technetium-99m with peak energy emission at 140 kev, a half-life of 6 hours and no beta emission. Unfortunately, present techniques available for coupling technetium-99m to macromolecules are harsh on the macromolecules since the technetium is normally reduced and coupled in an acid environment which may result in degradation of the protein macromolecule. For example, technetium-pertechnetat is normally reduced in an acid pH to $Tc^{+3}$ or $Tc^{+4}$ with a stannous reducing agent. The protein macromolecule then is added to the reduced form of technetium-99m in order to radiolabel the protein molecule. At the acid conditions under which this radiolabeling is conducted, a significant amount of the protein becomes degraded thereby significantly reducing the amount of useful radiolabeled protein that can be obtained.

It would be highly desirable to provide a method for radiolabeling proteins or other biological molecules which minimized or prevented the degradation of the protein or biological molecule. Specifically, it would be desirable to provide a means for radiolabeling such molecules with technetium-99m, without accompanying denaturation of the biological activities.

SUMMARY OF THE INVENTION

The present invention provides a method of radiolabeling proteins including antibodies, antigens, antibody fragments or the like which are useful in diagnosis without significant deactivation of the biological activities. The compositions comprise a chelating agent covalently coupled to the protein and a radioactive molecule bound by the chelating agent at about neutral pH. It has been found that the radiolabeled compositions of this invention can be prepared at neutral or slightly basic pH so that the protein macromolecule is not degraded during the radiolabeling procedure. The protein macromolecule first is covalently coupled to the chelating agent. Subsequently, the radioactive molecule is reduced with an alkalai metal dithionite which then is admixed with a buffer in order to attain a pH of at least about 7.0 up to about 9.0. The buffered solution containing the radioactive molecule then is admixed to the chelate coupled protein in order to radiolabel the chelate protein. The radiolabeled compound then can be utilized in vivo in order to test for a variety of physical conditions by scintigraphy. For example, when the protein macromolecule comprises antimyosin, the radiolabeled compound can be utilized to test for myocardial infarction. Similarly, when the protein macromolecule comprises anti-alpha feto protein or anti-CEA, the radiolabeled compound can be utilized to test for localization and visualization of malignant tumors or cancer cells. In addition, this invention includes a kit containing a protein antibody such as anti-myosin, anti-CEA, anti-alpha feto protein or the like, a chelating agent which is covalently linked to the antibody, alkalai metal dithinonite and a buffer. The kit also may include a chromatographic column capable of binding technetium as a pertechnetate.

DESCRIPTION OF SPECIFIC EMBODIMENTS

A bifunctional chelating agent such as diethylene triamine pentaacetic acid (DTPA), ethylene diamine, tetraacetic acid (EDTA) or the like is covalently coupled to the protein molecule by the carboxy carbonic anhydride reaction of the chelating agent with the protein molecule in the manner disclosed by Krejcarek and Tucker Biochem. Biophys. Res. Comm. 77:581 (1977). Generally, this method comprises formation of a peptide bond between protein and the chelate.

Representative suitable radioactive molecules which can be coupled to the chelating agent on the protein molecule include technetium-99m, indium-111, gallium-68 or -67, lead 203 or other multivalent cationic radioisotopes. The source of these radioactive molecules is well known and need not be described in detail herein. The invention will be described herein with reference to the use of technetium-99m as the radioactive molecule to be coupled to the chelating agent covalently bonded to the protein molecule at about neutral pH. Indium-111, gallium-68, -67, etc. require pH 3.5 for their solubility. Generally, technetium-99m is obtained from a conventional 99Mo/99mTc generator in order to obtain pharmaceutically acceptable technetium-99m. The technetium-99m generally is obtained from the generator in the oxidized form as the pertechnetate. In accordance with this invention, the oxidized form of the radiolabeled molecule is reduced with dithionite ion to produce a reduced pharmaceutically acceptable molecule containing the radioactive molecule desired. Representative suitable sources of dithionite include sodium dithionite (preferred), potassium dithionite and zinc dithionite. The reduction reaction can be conducted either in the presence of or in the absence of a buffer such as phosphate buffer. However, it is preferred to conduct the reaction with the dithionite in solid particulate form suspended in a solution of the pertechnetate. By operating in this manner, substantially all of the pertechnetate is reduced without being undesirably bound to the buffer utilized, e.g., phosphate buffer. Generally, the reduction reaction is conducted at a temperature between about 4° C. and about 37° C. while stirring vigorously. When operating without a buffer, the pH of the solution gradually increases from acidic to neutral as the reduction reaction proceeds. Therefore, the use of a buffer is not an absolute requirement in order to attain the desired neutral or slightly basic pH of the solution containing the reduced pertechnetate. The reduced technetium-99m is then chelated with DTPA-macromolecules and isolated from the reaction medium by any conventional means such as column chromatography.

Chelation of reduced $^{99m}Tc$ is instantaneous by chelate-protein covalent complex, but is incubate at room temperature for 5 to 10 minutes to ensure complete chelation. Generally, suitable incubation times are between about 1 min and about 5 minutes at normal room temperature. The temperature of incubation is such as to promote binding of the technetium-99m without denaturing the protein, usually between about 4° C. and about 37° C. The radiolabeled protein molecule then is recovered by elution through a chromatographic column. Representative suitable proteins which can be radiolabeled in accordance with this invention include myosin, anti-myosin, fibrinogen, anti-CEA, anti-alpha feto protein, anti-human chorionic gonadotropin, LDL and, all antibodies or the like. Chelation of the radioactive molecule is conducted with the pH of at least about 7.0 up to about 9, preferably between about 7.0 and 8.0. By operating in this manner, denaturation of the protein molecule due to solution pH is minimized or prevented. Therefore, the recovery of radiolabeled protein is maximized. The radiolabeled proteins of this invention can be utilized in vivo in order to provide visual reproductions of various portions of the body by conventional scintigraphy or utilized in vitro in conventional agglutination reactions by radioimmunoassay.

The present invention also can be utilized in kit form wherein the protein either unbound or bound to the chelating agent can be housed in a vial such as in lyophilized form or in an aqueous medium suitable buffered to minimize or prevent denaturation of the protein. If the vial containing the protein does not contain a buffer, a separate vial containing the buffer, such as a phosphate buffer can be provided. The dithionite either in liquid or solid form can be housed in a separate vial. In use, the dithionite is added to the oxidized molecule containing the radioactive label in order to effect reduction and the desired increase in pH. The reduced radioisotope then is added to the chelate-protein covalent complex to which has been previously added the buffer so that the radiolabel can be bound to the chelate portion of the chelated protein molecule. The radiolabeled chelate-protein molecule then can be purified in a second chromatographic column, which, if desired, can be provided with the kit. Representative suitable chromatographic purification materials include Sephadex, Chelex-100 or the like.

Generally, the radiolabeled chelate-protein can be administered by the intravenous or intracoronary route in a pharmaceutically acceptable saline solution. Representative suitable dosage is between about 10 and 20 millicuries, preferably about 15 millicuries for a normal kg patient.

EXAMPLE I

The following example illustrates the present invention and is not intended to limit the same.

Preparation of Anti Canine-Cardiac Myosin Fab Fragments

Rabbit anti-canine-cardiac myosin was prepared by myosin-Sepharose affinity chromatography of rabbit antiserum as described by Khaw and co-workers. Briefly, an aliquot of purified canine-cardiac myosin was obtained by the method of Katz and co-workers Circulation Research Vol. 19, Pgs 611–620, 1965. Purity was determined in 10% polyacrylamide SDS gel electrophoresis. The purified cardiac myosin was used to immunize rabbits in complete Freund's adjuvant. Another aliquot of myosin was used to prepare a myosin-Sepharose-4B column by the cyanogen bromide activation procedure of Cuatrecassa. Rabbit antiserum was applied to the affinity column and non-antibody serum components eluted with 0.3 M PBS pH 7.0. Anti-myosin antibody was desorbed from the myosin-Sepharose column with 5 M guanidine. Renaturation was achieved by serial dialysis in 3 M KCl then against 0.3 M PBS. The renatured Ab was then tested for the antibody activity by the binding capacity for the homologous iodine-125 labeled canine-cardiac myosin.

Fab fragments of anti-myosin antibody were prepared by papain digestion at enzyme to substrate ratio of 1:100 at 37° C. for 1½ hr. Fab fragments were separated from Fc fragments and undigested whole antibody by Protein-A Sepharose affinity chromatography. Fc and whole antibody were bound by Protein-A column, whereas Fab fragments were recovered in the fall-through fraction. Purity of Fab fragments was indicated by partial identity against whole Ab and precipitin lines of non-identity against Fab fragments. Fab fragments were concentrated by vacuum dialysis to 4 or 5 mg/ml, then dialyzed against 0.1 M $NaHCO_3$ and frozen until used.

Covalent Coupling with DTPA

A bifunctional chelating agent, diethylene triamine pentaacetic acid (DTPA) was covalently coupled to either AbFab or Fibrinogen by the carboxy carbonic anhydride reaction of DTPA by the method of Krejcarek and Tucker Biochem. Biophys. Res. Comm. 77:581 (1977) (BBRC 1977). The concentrations for use were adjusted to covalently coupling DTPA to small amounts of protein, where it was desirable to use 4 or 5 mg/ml solution in order to obtain efficient carbonic anhydride coupling.

Following covalent coupling of DTPA to anti-myosin Fab fragments, the antibody activity of DTPA-Ab-Fab was compared to unmodified AbFab for the $^{125}I$-labeled homologous antigen. The lactoperoxidase procedure of Marchalonis was employed to iodinate canine-cardiac myosin with iodine-125. Free and bound $^{125}I$-canine-cardiac myosin was separated by the use of a second goat antirabbit IgG antiserum. The covalent coupling of DTPA to AbFab did not cause denaturation of the AbFab. The binding capacity for $^{125}ICCM$ by DTPA-AbFab and AbFab were not significantly different from each other.

Chelation of Reduced $^{99m}Tc$ by DTPA-Ab Fab or DTPA Fibrinogen

Generator eluted $^{99m}Tc$-pertechnetate (NEN) was reduced with sodium dithionite ($Na_2S_2O_4$). $Na_2S_2O_4$ reduced $^{99m}Tc$ is added to DTPA-Ab-Fab or DTPA-Fibrinogen (100–200 μg) in 0.3 M phosphate buffered saline (pH 7.0) while stirring vigorously. Chelated $^{99m}Tc$ and free $^{99m}Tc$ were separated by Sephadex G25 column chromatography (0.5 × 10 cm).

Clotability and Precipitability of $^{99m}Tc$-DTPA-Fibrinogen (a) Clotability of whole blood: To 1 cc of fresh human blood from a volunteer, 100 μCi of $^{99m}Tc$-DTPA-Fib. were added or 100 μCi of $^{125}I$-Fib were added and incubated at RT. overnight. Serum was separated by centrifugation and serum and particulate material counted in a gamma well counter.

(b) Clotability in plasma (dog): To 0.5 ml of fresh dog plasma, 10 μl of $^{99m}Tc$-DTPA-Fib (10 μCi) or 10 μl $^{125}I$-Fibrinogen (1 μCi) were added. The plasma was allowed to clot and the serum separated by centrifugation. The supernatant and the precipitant were counted in a gamma counter.

(c) Clotability in old human plasma with thrombin: To 200 μg aliquots of DTPA-Fibrinogen, 10λ of $^{99m}I$-

Fib were added. Then 0.5 ml of human plasma in citrate (from MGH Blood Bank) was added and then 10 units of thrombin added to the above mixture. The mixture was allowed to clot at room temperature for 2 hr after which the clot was washed 2 times with 1 ml 0.3 M PBS. Supernatant and wash were separated from clot by centrifugation and then counted in a gamma counter.

Clotability was calculated as $^{99m}$Tc activity in the clot to total activity in the reaction mixture.

Experimental Myocardial Infarction

Dogs (n=8) were anesthetized with intravenous pentobarbiton injections followed by left thoracotomy. The left anterior descending coronary artery was dissected free from surrounding tissues approximately ⅔ the distance from apex to base and was occluded with a silk ligature. In 4 dogs, the ligature was left in place and the thoracotomy closed. The animals were allowed to recover. At 4 hr coronary occlusion, 8–10 mCi of $^{99m}$Tc-DTPA-AbFab were injected intravenously. Scintigraphy was performed using a portable Ohio Nuclear camera or an Ohio Nuclear Series 100 Anger camera equipped with a low energy collimator. 10 minute counts containing greater than $5 \times 10^5$ counts were obtained. The earliest "hot spot" localization was obtained at 12 hr post IV injection of the Ab. Experimental Ml was confirmed by histochemical Triphenyltertazoliem chloride staining which stains for dehydrogenase activity in normal myocardium. Following sacrifice, the heart was excised, cut into ventricular slices parallel to the atrioventricular groove and reimaged for 100,000 counts. The hot spot imaging was to compare to histochemically delineated infarction.

The other group of 4 dogs were subjected to 1 hr of LAD occlusion followed by reperfusion by removal of the occlusive ligature. 5 minutes before reperfusion, $1 \times 10^6$ radiolabeled carbonized microspheres (10–15μ) were injected directly into the left atrium to determine relative regional myocardial blood flow and 15 minutes after reperfusion 1–5 m Ci of $^{99m}$Tc-DTPA-Fibrinogen (≃100 μg) were injected intravenously. 2 hr post IV injection, the dogs were sacrificed and histochemically stained with TTC. The hearts were excised and cut into epi- and endocardial biopsies of 0.5 to 1 g pieces and were counted in an automatic gamma counter (Packard) and relative distribution of Fibrinogen and microspheres calculated. Regional blood flow was determined as % activity of normal myocardium and relative Fibrinogen uptake was determined as $^{99m}$Tc. Fibrinogen in test myocardium/$^{99m}$Tc Fibrinogen in normal myocardium.

To 10–21 mCi of $^{99m}$TcO$^-_4$, 1 mg/mCi of Na$_2$SO$_4$ was added and incubated in a closed vesicle for 5 to 10 minutes at room temperature. To 100–200 μg of DTPA-AbFab of DTPA-Fibrinogen, in 250 μl of 0.3 M phosphate pH 7.0, 0.15 M NaCl, the reduced $^{99m}$Tc was added while stirring vigorously. This was immediately followed by addition of 250 μl of 0.3 M phosphate buffer solution (PBS). The total pH change was not significantly different from that of the starter buffer. After 10 minutes of incubation at room temperature, bound and free $^{99m}$Tc were separated by Sephadex G-25 column chromatography (1×10 cm). $^{99m}$Tc chelated to proteins were eluted in the void volume. To further demonstrate that $^{99m}$Tc activity in the void volume is associated with the protein, to a precalibrated Sepharose 4B column, an aliquot of $^{99m}$Tc-DTPA-AbFab was applied and eluted with 0.3 M PBS. Standards used for calibration were blue dextran to show the void volume, normal 1 gG and $^{125}$I-Ab (Fab')2 and BSA. The elution profiles demonstrating that $^{99m}$Tc-DTPA-AbFab is eluted in the region of 50,000 daltons molecular weight species.

To further demonstrate that the anti-myosin antibody activity is retained following labeling of DTPA-Ab-Fab with reduced $^{99m}$Tc, an aliquot of $^{99m}$Tc-ABFab recovered in the void volume of Sephadex G-25 column chromatography, was applied to a myosin-Sepharose 4 B (3 ml) affinity column. Denatured Ab and non-chelated $^{99m}$Tc activity were eluted in the wash through fraction and specific $^{99m}$Tc-DTPA-AbFab is eluted with 5 M Guanidine HCl. Approximately 90% of the $^{99m}$Tc activity applied to the column was associated with AbFab which is retained by the affinity column demonstrating that the method developed for reduction and chelation of $^{99m}$Tc to DTPA-AbFab was gentle and caused very little denaturation.

To test for the biological activity of $^{99m}$Tc-DTPA-Fibrinogen, 100 μl containing 100 μCi/4.49 μg Fibrinogen were added to 1 ml of fresh blood. As control $^{125}$I-Fibrinogen was also added to 1 ml of fresh blood. The mixtures were allowed to clot at room temperature overnight. The clot was separated from supernatant solution by centrifugation and the radioactivity distribution calculated after scintillation counting. Table I shows that approximately 76% of total activity was associated with the clot. Table I also shows that $^{99m}$-Tc-DTPA-Fibrinogen was (a) still clotable in fresh dog plasma; (b) clotable by addition of thrombin in presence of added DTPA-Fibrinogen and (c) in pooled normal human plasma in citrate and 10 units of thrombin. These results indicate that the method development for labeling of $^{99m}$Tc to to biologically active macromolecules does not cause appreciable denaturation of these biomolecules.

To demonstrate precipitability of $^{99m}$Tc-DTPA-Fibrinogen, 100 μl $^{99m}$-Tc-DTPA-Fibrinogen (4.4 μg) was added to 200 μg of DTPA-Fibrinogen and then a saturated (NH$_4$)$_2$SO$_4$ added to give a final conc. of 25% (NH$_4$)$_2$SO$_4$ saturation. Precipitate was washed 2 times with 25% (NH$_4$)$_2$SO$_4$ and supernatant and precipitate counts determined in a scintillation counter. Table II shows that approximately 80% of the radioactivity was associated with precipitable Fibrinogen.

To test for the biological activities of $^{99m}$Tc-DTPA-AbFab in vivo, dogs with coronary artery occlusion were employed as described above. A left lateral and anteroposterior scintigram showed localization of $^{99m}$Tc-DTPA-AbFab in the anteroapical region of the heart which was the site of experimental infarcation. Central liver activity is also observed due to presence of some denatured proteins. The data showed that reduction of blood flow for 1 hr effected vascular damage causing fibrinolosis and blood clot formation. The results indicated that in vivo biological activities of $^{99m}$Tc-DTPA-AbFab and $^{99m}$Tc-DTPA-Fibrinogen were preserved following labeling of these proteins with technetium-99m.

TABLE I

| CLOTABILITY OF $^{99m}$Tc-DTPA FIBRINOGEN | | | | |
|---|---|---|---|---|
| Sample | Time | Radio-Labeled Fibrinogen | Carrier Fibrinogen | % Activity in Clot ± SD |
| 1. Fresh Human Blood | 24 hr. | $^{99m}$Tc | — | 77.8 ± 0.3 |

TABLE I-continued

CLOTABILITY OF $^{99m}$Tc-DTPA FIBRINOGEN

| Sample | Time | Radio-Labeled Fibrinogen | Carrier Fibrin-ogen | % Activity in Clot ± SD |
|---|---|---|---|---|
| 2. Fresh Human Blood | 24 hr. | $^{125}$I | — | 44.2 ± 3.7 |
| 3. Human Plasma | 2 hr. | $^{99m}$Tc | — | 57.3 ± 8.7 |
| 4. Human Plasma | 2 hr. | $^{125}$I | — | 76.0 ± 2.1 |
| 5. Human Plasma (Citrated & Thrombin) | 2 hr. | $^{99m}$Tc | — | 77.6 ± 4.8 |
| 6. Human Plasma (Citrated & Thrombin) | 2 hr. | $^{125}$I | | 77.9 ± 7.4 |
| 7. Dog Blood (Fresh) | 2 hr. | $^{99m}$Tc | | 31.6 ± 0.8 |
| 8. Dog Blood (Fresh) | 2 hr. | $^{125}$I | | 66.3 ± 2.3 |
| 9. Dog Plasma | 2 hr. | $^{99m}$Tc | | 37.5 ± 2.2 |
| 10. | | $^{125}$I | | 63.6 ± 1.9 |
| 11. Dog Plasma & Thrombin | 2 hr. | $^{99m}$Tc | | 57.0 ± 5.4 |

TABLE II $^{99m}$Tc ASSOCIATED WITH PRECIPITABLE FIBRINOGEN

| $^{99m}$Tc-DTPA-Fibrinogen | Carrier DTPA Fibrinogen | 100% $(NH_4)_2SO_4$ | % ppd |
|---|---|---|---|
| 1. 100λ (4.4 μg) | 200 μg (200 μl) | 150λ | 80% |
| 2. 200λ ( | (1.25 mg) (100λ) | 180λ | 81.7 ± 3. |
| 3. $^{125}$I Fibrinogen (NEN) (200λ) | 1.25 mg (100λ) | 100λ | 92.9 ± 0 |

We claim:

1. A composition comprising a protein covalently bonded to a bifunctional physiologically acceptable chelating agent and technetium-99m being bound to said chelating agent, said technetium-99m being reduced with dithionite and mixing said technetium-99m with said protein covalently linked to said chelating agent at a pH of at least about 7.0 up to about 9.0.

2. The composition of claim 1 wherein said chelating agent is diethylene triamine pentaacetic acid.

3. The composition of claim 1 wherein said chelating agent is diethylene triamine pentaacetic acid.

4. The composition of any one of claims 1, 2 or 3 wherein said protein is anti-myosin.

5. The composition of any one of claims 1, 2 or 3 wherein said protein is fibrinogen.

6. The composition of any one of claims 1, 2 or 3 wherein said protein is anti-carcinoembryonic antigen.

7. The composition of any one of claims 1, 2 or 3 wherein said protein is anti-alpha feto protein.

8. The composition of any one of claims 1, 2 or 3 wherein said protein is anti-human chorionic gonadotropin.

9. The process of forming the composition of claim 1 which comprises reducing an oxidized form of said radioactive molecule with dithionite ion to obtain a reduced form of said radioactive molecule and mixing said radioactive molecule with said protein covalently linked to said chelating agent at a pH of at least about 7.0 up to about 9.0.

10. The process of claim 9 wherein said pH is between about 7.0 and 8.0.

11. The process of claim 9 wherein the source of said dithionite ion is sodium dithionite.

12. The process of claim 10 wherein the source of said dithionite ion is sodium dithionite.

13. The process of any one of claims 10, 11 or 12 wherein the oxidized form of the radioactive molecule is pertechnetate ion which is reduced to technetium-99m ion.

14. The process of any one of claims 10, 11 or 12 wherein the source of dithionite ion is particulate sodium dithionate.

* * * * *